United States Patent
Nelson, Jr.

(10) Patent No.: US 9,261,457 B1
(45) Date of Patent: Feb. 16, 2016

(54) LASER ABSORPTION MEASUREMENT FOR CLUMPED ISOTOPES

(71) Applicant: Aerodyne Research, Inc., Billerica, MA (US)

(72) Inventor: David D. Nelson, Jr., N. Chelmsford, MA (US)

(73) Assignee: Aerodyne Research, Inc., Billerica, MA (US)

(*) Notice: Subject to any disclaimer, the term of this patent is extended or adjusted under 35 U.S.C. 154(b) by 0 days.

(21) Appl. No.: 14/538,510

(22) Filed: Nov. 11, 2014

(51) Int. Cl.
  *G01N 21/00* (2006.01)
  *G01N 21/39* (2006.01)
  *G01N 33/00* (2006.01)

(52) U.S. Cl.
  CPC ............ *G01N 21/39* (2013.01); *G01N 33/0062* (2013.01); *G01N 2201/06113* (2013.01); *G01N 2201/125* (2013.01)

(58) Field of Classification Search
  CPC ............... G01N 2333/726; G01N 2500/04; G01N 2500/00; G01N 33/5041; G01N 33/5058; G01N 33/6893; G01N 33/74; G01N 2333/495; G01N 33/6872; G01N 1/405; G01N 2030/009; G01N 2030/062; G01N 21/553
  See application file for complete search history.

(56) References Cited

U.S. PATENT DOCUMENTS

| | | | |
|---|---|---|---|
| 3,893,771 A | 7/1975 | Bell | |
| 4,990,780 A * | 2/1991 | Lee | G01N 21/39 250/339.13 |
| 5,110,430 A * | 5/1992 | Eerkens | B01J 19/121 204/157.2 |
| 5,308,979 A * | 5/1994 | Villa-Aleman | H01J 49/0422 250/288 |
| 5,957,858 A * | 9/1999 | Micheels | G01N 21/3504 250/339.03 |
| 8,595,020 B2 | 11/2013 | Marino | |
| 8,823,923 B2 * | 9/2014 | Berman | G01N 21/031 356/39 |
| 2009/0026362 A1 * | 1/2009 | Arii | G01N 27/64 250/281 |
| 2010/0198736 A1 * | 8/2010 | Marino | G01N 21/3504 705/308 |
| 2011/0212536 A1 * | 9/2011 | Krummen | G01N 30/462 436/161 |

OTHER PUBLICATIONS

Eiler, John M., "'Clumped-isotope' geochemistry—The Study of Naturally-Occurring, Multiply-Substituted Isotopolgues," ScienceDirect, Elsevier B. V., Earth and Planetary Science Letters, 262, Aug. 28, 2007, pp. 309-327.

Mcmanus, J. B., et al., "A High Precision Pulsed Quantum Cascade Laser Spectrometer for Measurements of Stable Isotopes of Carbon Dioxide," Journal of Modern Optics, vol. 52, No. 16, Nov. 10, 2005, pp. 2309-2321.

(Continued)

*Primary Examiner* — Michael P Stafira
(74) *Attorney, Agent, or Firm* — Cesari and McKenna, LLP; James A. Blanchette

(57) ABSTRACT

In one embodiment, an apparent equilibrium constant involving a clumped isotope in a gaseous sample is measured by acquiring sample spectra of portions of the gaseous sample at different pressures. An external bulb coupled to a sample cell is filled with the gaseous sample. A first portion of the gaseous sample is transferred from the external bulb to the sample cell, where it is at a first pressure. A first sample spectrum is obtained. Then, a second portion of the gaseous sample is transferred from the external bulb to the sample cell, where it is at a second, different pressure. A second sample spectrum is obtained. An apparent equilibrium constant for the clumped isotope is calculated by determining a first isotopic ratio at the first pressure, determining a second isotopic ratio at the second pressure, and taking a product of the first isotopic ratio and the second isotopic ratio.

26 Claims, 5 Drawing Sheets

(56) References Cited

OTHER PUBLICATIONS

Nelson, David D., et al., "New Method for Isotopic Ration Measurements of Atmospheric Carbon Dioxide Using a 4.3 μm Pulsed Quantum Cascade Laser," Springer-Verlag, Jan. 19, 2008, pp. 1-23.

Saleska, Scott R., et al., "What are the Instrumentation Requirements for Measuring the Isotopic Composition of Net Ecosystem Exchange of $CO_2$ Using Eddy Covariance Methods," Isotopes in Environmental and Health Studies, Dec. 2005, pp. 1-39.

* cited by examiner

LASER ABSORPTION MEASUREMENT FOR CLUMPED ISOTOPES

BACKGROUND

1. Technical Field

The present disclosure relates generally to isotope measurement, and more specifically to techniques for using spectrometry to measure an apparent equilibrium constant involving a clumped isotope.

2. Background Information

Isotopologues are species of a molecule that differ in the isotopic identity of one or more of their constituent atoms. For example, $^{14}N^{14}N$, $^{15}N^{14}N$ and $^{15}N^{15}N$ are three isotopologues of a nitrogen diatomic molecule. Multiply-substituted isotopologues, commonly referred to simply as "clumped isotopes", are isotopologues that contains two or more rare isotopes. For example, $^{12}C^{16}O^{17}O$, $^{13}C^{16}O^{17}O$, and $^{13}C^{16}O^{18}O$ are examples of clumped isotopes of carbon dioxide. By analyzing the relative abundances of these isotopes, or more specifically equilibrium constants involving clumped isotopes governing the formation of a sample, various types of useful information may be determined. Among other things, they may provide the formation temperature of the sample.

Traditionally, measurements of the relative abundances of clumped isotopes have been performed using mass spectrometers. More recently, attempts have been made to utilize instruments (e.g., isotope monitors) that include laser absorption spectrometers. FIG. 1 is a generalized block diagram of an example instrument 100. The example instrument includes a laser 110, a sample cell 120 having valved gas inlet and gas outlet ports 122, 124, and a light detector 130. A gaseous sample to be analyzed is fed into the sample cell by opening a valve of the gas inlet port 122. A laser beam 112 is then emitted from the laser 110 and enters the sample cell 120 through an entrance window 126. The laser beam 112 interacts with the gaseous sample, and may be partially absorbed by the gas. A remaining portion of the laser beam 112 emerges from an exit window 124, where it is detected by the light detector 130. The light detector converts the detected laser light to an electrical voltage.

The isotope monitor utilizes a computing system 140 that monitors the electrical voltage returned from the light detector. The computing system 140 may communicate with the laser 110 and direct it to change the wavelength of the laser beam within a given range to probe various spectroscopic lines being studied.

FIG. 2 is a plot showing species of a carbon dioxide sample measured using the example instrument of FIG. 1. The species include $^{12}C^{16}O^{16}O$ (abbreviated "626"), $^{13}C^{16}O^{16}O$ (abbreviated "636"), $^{12}C^{16}O^{18}O$ (abbreviated "628"), $^{12}C^{16}O^{17}O$ (abbreviated "627"), the clumped isotope $^{13}C^{16}O^{18}O$ (abbreviated "638"), the clumped isotope $^{13}C^{16}O^{17}O$ (abbreviated "637"), and the clumped isotope $^{12}C^{8}O^{18}O$ (abbreviated "828"). While all required species are present in FIG. 2, the dynamic range is larger than desired. For example, the spectroscopic line strengths of the major species 636 and the clumped isotope 638 have a ratio of 40:1. This may present various challenges. For example, if the major specie's absorbance is constrained to less than 1 during testing to avoid saturation of optical absorbance, then 638 absorption will be constrained to be less than 2.5%. A spectroscopic line with 2.5% absorbance must be measured at extremely low noise levels (which are difficult to achieve with conventional instruments) to yield desirable levels of sensitivity. Greater sensitivity may be possible if absorbance could be constrained to a range of 0.1 to 1.0 for all required species. However, achieving more uniform absorbance among all required species presents a significant challenge.

Accordingly, there is a need for improved techniques for using laser absorption spectrometry to measure relative abundances of clumped isotopes, or more specifically equilibrium constants involving clumped isotopes.

SUMMARY

In one example embodiment, an improved instrument (e.g., a clumped isotope monitor) measures an apparent equilibrium constant a clumped isotope of a molecule (e.g., $CO_2$) in a gaseous sample by acquiring sample spectra of portions of the gaseous sample at different pressures. By taking measurements at different pressures, pressure reduction may be utilized to constrain absorbance (e.g., to a range of 0.1 to 1.0 for all required species). Pairs of isotopic ratios determined at different pressures may be combined to calculate the apparent equilibrium constant of the clumped isotope.

In one embodiment, the improved instrument utilizes an external bulb that initially holds the entire gaseous sample. The external bulb is coupled to the sample cell of a laser absorption spectrometer. As part of a measurement cycle, a first portion of the sample is transferred from the external bulb to the sample cell (e.g., allowed to expand from the external bulb into an evacuated sample cell), where it is at a first pressure. A first sample spectrum is obtained. Then, a second portion of the gaseous sample is transferred from the external bulb to the sample cell (e.g., allowed to expand from the external bulb into a newly evacuated sample cell), where it is at a second pressure (e.g., a reduced pressure in comparison to the first pressure). A second sample spectrum is obtained. A calculation technique is applied to the results from the two sample spectrum to determine the apparent equilibrium constant of the clumped isotope in the sample. The calculation technique determines the apparent equilibrium constant for the clumped isotope by determining a first isotopic ratio at the first pressure, determining a second isotopic ratio at the second pressure, and calculating the product of the first isotopic ratio and the second isotopic ratio.

With the measurement cycle and calculation technique, the improved instrument may achieve more uniform absorbance among disparate species, while avoiding saturation of optical absorbance by the major species. Fractionation may be avoided by, among other things, maintaining the gaseous sample at very low pressures, and transferring a large fraction of the sample from the external bulb to the sample cell. Further, steps of the measurement cycle may be executed rapidly, providing a relatively quick cycle time.

It should be understood that the example embodiments discussed in this Summary may include a variety of other features, including other features discussed below, and variations thereof. Further a variety of other example embodiments may be utilized. This Summary is intended simply as a brief introduction to the reader, and does not imply that the specific features mentioned herein are all the features of the invention, or are essential features of the invention.

BRIEF DESCRIPTION OF THE DRAWINGS

The text refers to the accompanying drawings, of which.

DESCRIPTION

Figure 1:
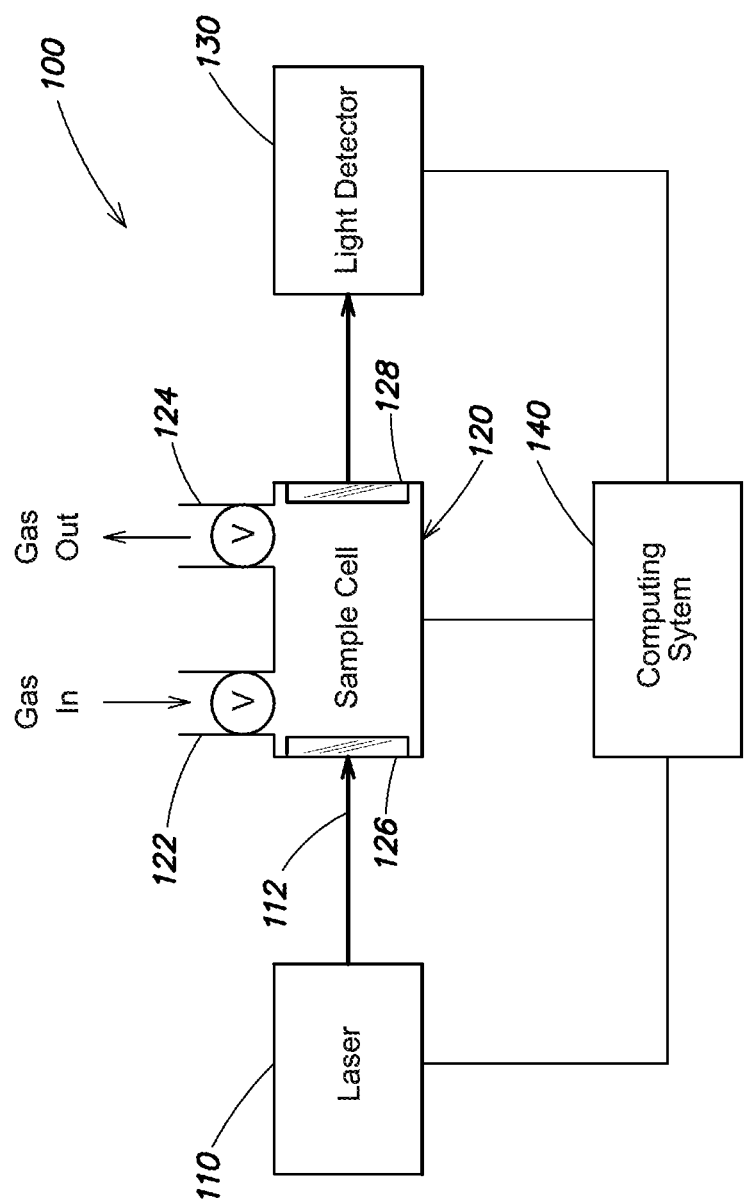
FIG. 1 is a generalized block diagram of an example instrument.
Figure 2:
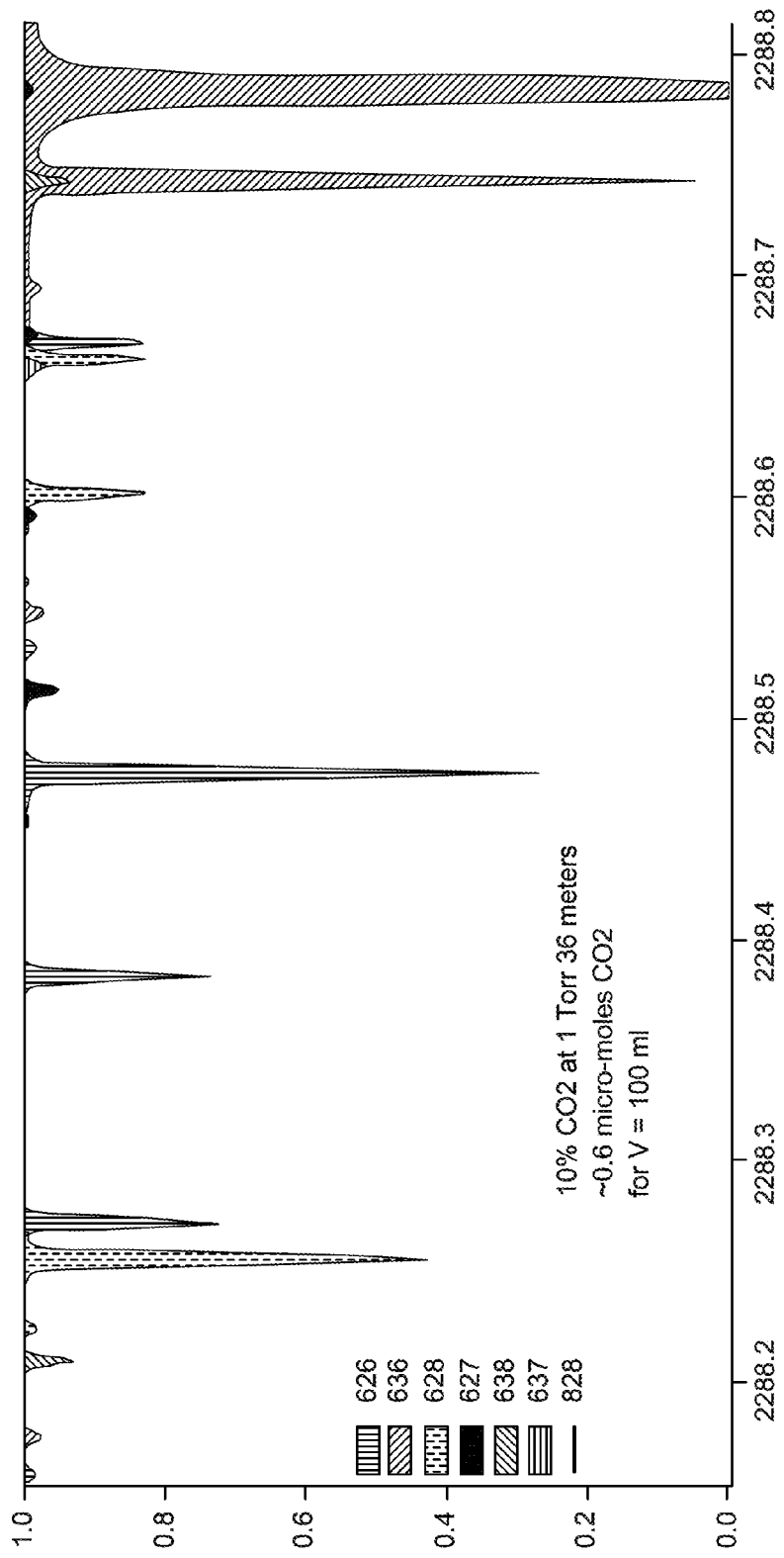
FIG. 2 is a plot showing species of a carbon dioxide sample measured using the example instrument of FIG. 1.
Figure 3:
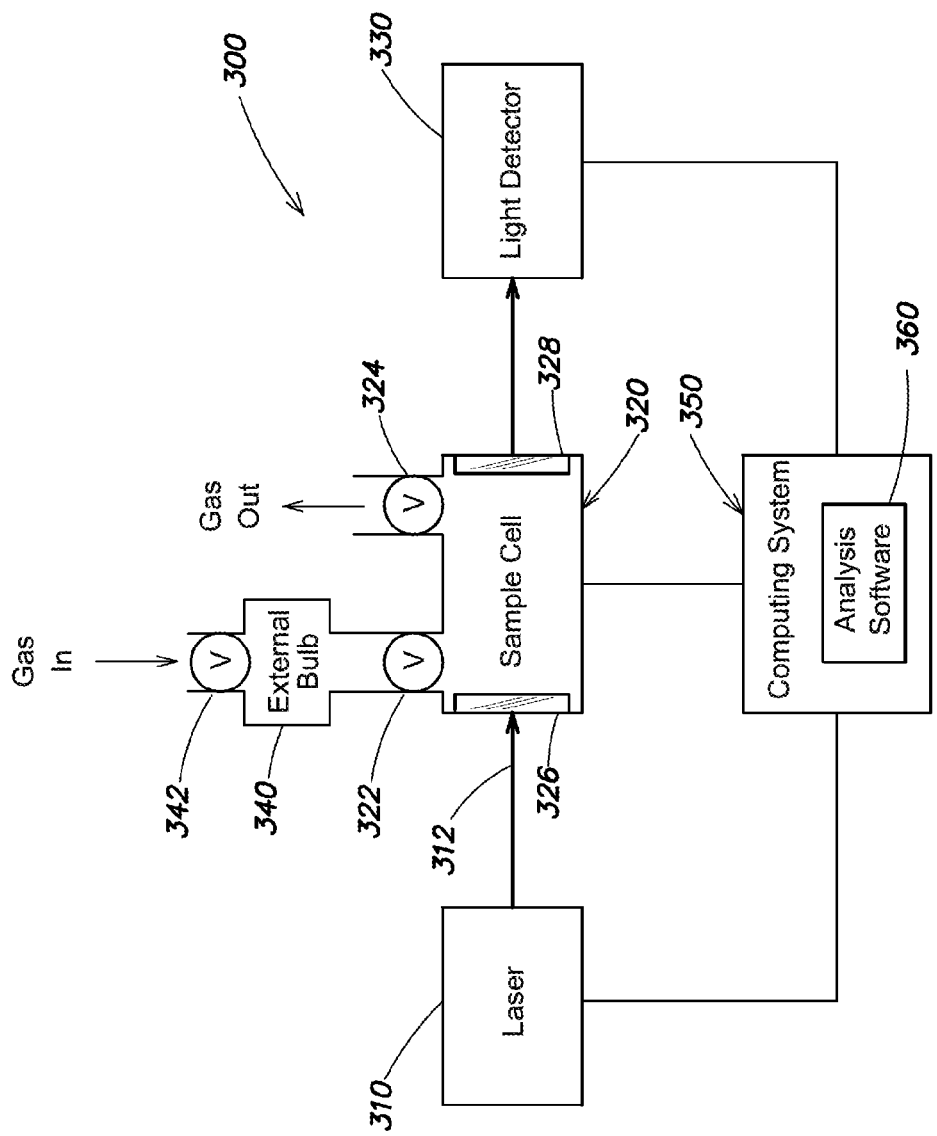
FIG. 3 is a generalized block diagram of an example improved instrument (e.g., a clumped isotope monitor)

FIG. 3 is a generalized block diagram of an example improved instrument (e.g., a clumped isotope monitor) 300. The instrument includes a laser absorption spectrometer having a laser 310, a sample cell 320 and a light detector 330. The laser absorption spectrometer may utilize a variety of different types of spectroscopy including, for example, direct absorption spectroscopy, cavity ring down spectroscopy, integrated cavity output spectroscopy, cavity enhanced absorption spectroscopy, etc. In one embodiment, the laser 310 may be a dual laser, having laser emitters operating at different frequencies (e.g., near 2288 and 2310 reciprocal centimeters ($cm^{-1}$)). However, it should be understood that a variety of other types of optical energy sources may be utilized. The sample cell 320 includes entrance and exit windows 326, 328, through which a laser beam 312 emitted by the laser 310 can pass, as well as valved gas inlet and outlet ports 322, 324. In one implementation, the sample cell has a volume of 100 milliliters (ml). However, it should be understood that a variety of other volumes are possible.

An evacuation pump (not shown) is coupled to the sample cell 320, for example, to the gas outlet port 324, and may be used to evacuate the sample cell, and by extension, any cavities coupled to the sample cell 320. A light detector 330 is positioned behind the exit window 328 to detect laser light that is not absorbed within the sample cell, and to convert the detected laser light to an electrical voltage that can be analyzed.

An external bulb 340, having its own valved gas inlet port 342, is coupled to the gas inlet port 322 of the sample cell 320. The volume of the external bulb may be substantially less than (e.g., an order of magnitude less than) the volume of the sample cell. In one implementation, the external bulb has a volume of 11 ml. However, it should be understood that a variety of other volumes are possible. Via that inlet port 342, a gaseous sample to be analyzed may be fed into the external bulb 340. The gaseous sample may be isolated in the external bulb by closing the valve on the inlet port 322 on the sample cell 320. By opening the valve on the inlet port 322 on the sample cell 320, the external bulb 340 may be connected to the sample cell 320 such that a portion of the gaseous sample may be transferred thereto (e.g., by expansion into an evacuated sample cell).

A computing system 350 is coupled to the other components of the example improved instrument 300, and includes a processor executing analysis software 360 that is capable of controlling (e.g., opening and closing) the valves on the ports 322, 324, 342, activating the evacuation pump, operating the laser 310 (e.g., directing it to probe various spectroscopic lines), and monitoring the electrical voltage returned from the light detector 330, among other types of control and monitoring. As explained in more detail below, the control and monitoring operations may be conducted according to a measurement cycle. The analysis software may further apply a calculation technique to determine an apparent equilibrium constant based on data collected during one or more measurement cycles. As used herein the term "apparent equilibrium constant" refers to a value that is believed to be an equilibrium constant, but that may require further testing to verify it was formed at equilibrium. An apparent equilibrium constant may be represented as a "super ratio" expressed as the ratio (or product) of two isotopic ratios divided, or an equivalent expression.

Figure 4:
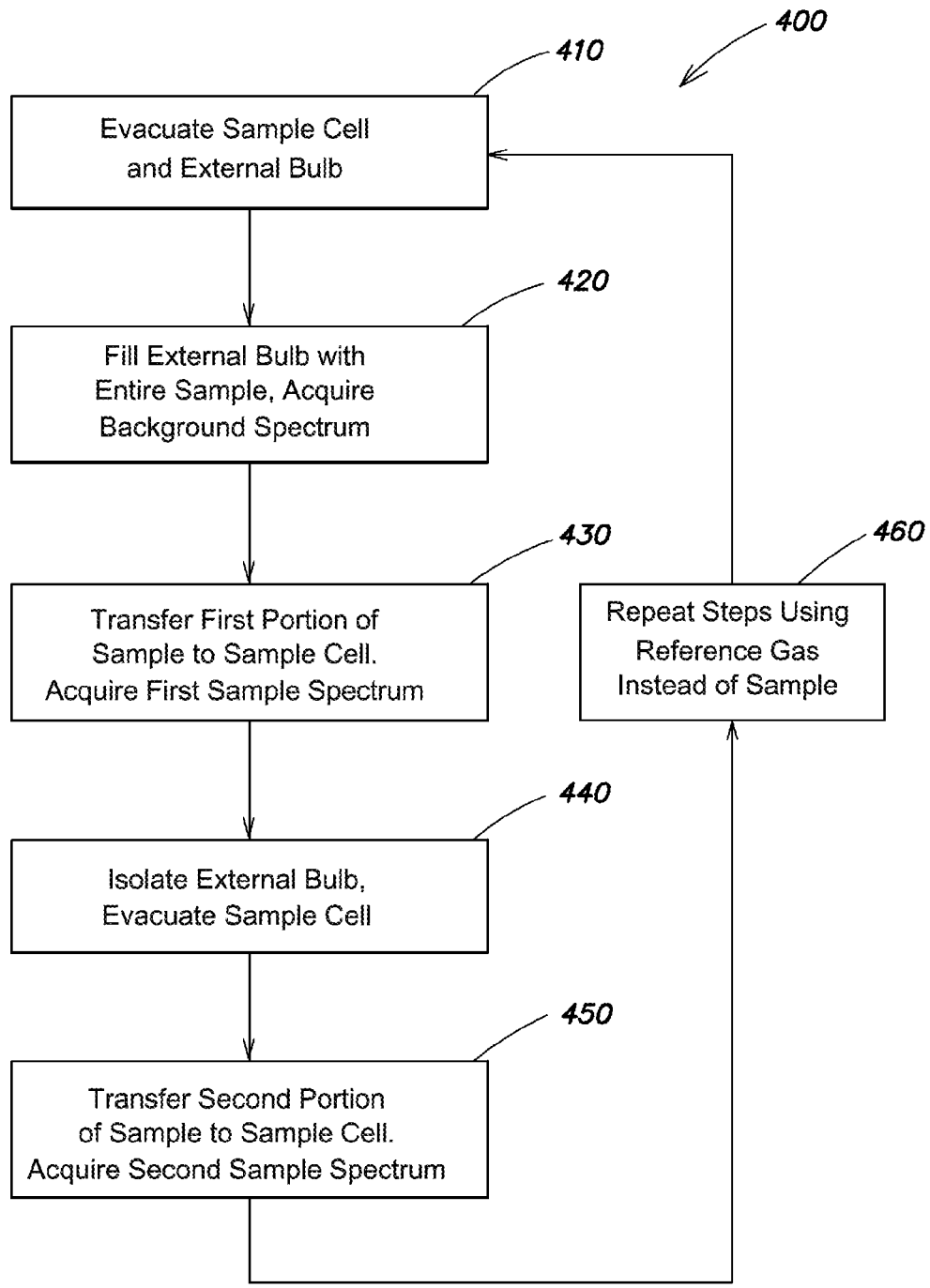
FIG. 4 is a flow diagram of a sequence of steps for an example measurement cycle using the example improved instrument.

FIG. 4 is a flow diagram of a sequence of steps for an example measurement cycle 400 using the example improved instrument 300. The molecule studied may be carbon dioxide, methane, nitrous oxide, carbon monoxide, or another molecule of interest. The clumped isotope(s) being studied may vary depending on the molecule being studied.

Steps of the example measurement cycle 400 may be executed rapidly, providing a relatively quick cycle time. In one implementation, the cycle time may be approximately 12 minutes. In comparison, a typical cycle time for isotope ratio mass spectrometry is 3 to 4 hours. Example times of each step of the cycle are provided in the discussion below. It should be understood, however, that such times are merely for purposes of illustration, and that the exact times for each step, and the measurement cycle as a whole, will vary depending on the exact components of the example improved instrument 300, and/or the molecule being studied.

At step 410, the analysis software 360 executing on the computing system 350 readies the instrument 300 for use by evacuating the external bulb 340 and sample cell 320 (e.g., to a pressure of $10^{-6}$ millibars (mbar)), for example, activating the evacuation pump (not shown). The operations of step 410 may take approximately 30 seconds.

At step 420, the analysis software 360 fills the external bulb 340 with the entire gaseous sample to be analyzed. For example, the analysis software 360 may close the valve on the gas inlet port 322 to isolate the external bulb 340 from the sample cell 320, and operate the valve of the via gas inlet port 342 to fill the external bulb 340 with the entire gaseous sample to be analyzed. In one implementation, a 1 micro-mole (kmol) sample is used, and the external cell 340 is filled to a pressure (herein an "initial sample pressure") of approximately 2 mbar. While a variety of different sizes and pressures may be utilized, certain advantages may be achieved by operating at very low pressures, as discussed in more detail below.

Also, at step 420 (e.g., simultaneous to filling the external bulb 340), the analysis software 360 controls the laser 310, and monitors the light detector 330, to acquire a background spectrum using the evacuated sample cell 320. In total, the operations of step 420 may take approximately 100 seconds.

At step 430, the analysis software 360 transfers a first portion of the gaseous sample from the external bulb 340 to the sample cell 320, and acquires a first sample spectrum of the first portion of the gaseous sample. For example, the analysis software 360 may open the gas inlet port 322 of the sample cell 320 and allow the gaseous sample to expand into the evacuated sample cell 320. The resulting pressure in the sample cell (referred to as the "first pressure"), may be an order of magnitude lower than the initial sample pressure. Given the above described example volumes and pressures, the first pressure may be approximately 0.2 mbar. In an implementation where the laser 310 is a dual laser, the first sample spectrum may be acquired using one of the two lasers. In total, the operations of step 430 may take approximately 100 seconds.

At step 440, the analysis software 360 closes the valve on the gas inlet port 322 to isolate the external bulb 340 from the sample cell 320. The isolated external bulb 340 holds a remaining part of the gaseous sample (e.g., at a pressure of 0.2 mbar). The analysis software 360 further evacuates the sample cell 320 (e.g., to a pressure of $10^{-6}$ mbar), for example, utilizing the evacuation pump (not shown). The operations of step 440 may take approximately 30 seconds.

At step 450, the analysis software 360 executing on the computing system 350 transfers a second portion of the gaseous sample from the external bulb 340 to the sample cell 320, and acquires a second sample spectrum of the second portion of the gaseous sample. For example, the analysis software may open the gas inlet port 322 of the sample cell 320 and allow the remaining part of the gaseous sample to expand into the evacuated sample cell 320. The resulting pressure in the sample cell (referred to as the "second pressure") may be an order of magnitude lower than was the case when the first gaseous sample was in the sample cell. Given the above described example volumes and pressures, the second pressure may be approximately 0.02 mbar. In an implementation where the laser 310 is a dual laser, the second sample spectrum may be acquired using a different one of the two lasers than the one that captured the first sample spectrum. In total, the operations of step 450 may take approximately 100 seconds.

At step 460, the operations of steps 410-450 are repeated using a reference gas in place of the gaseous sample. The results of such repeated steps may be used for calibration, according to techniques known to those skilled in the art. In total, the operations of step 460 may take approximately 360 seconds. Thereafter, execution may loop back to step 410, and the measurement cycle 400 repeated for successive gaseous samples (e.g., such that averaging may be utilized to increase measurement accuracy).

By applying a calculation method to the results of the measurement cycle 400, the analysis software 360 executing on the computing system 350 may determine isotopic ratios of specific isotopologues of a molecule in the gaseous sample, including an isotopic ratio involving the clumped isotope. The product of these ratios may form a super ratio which may be interpreted as an apparent equilibrium constant.

Figure 5:
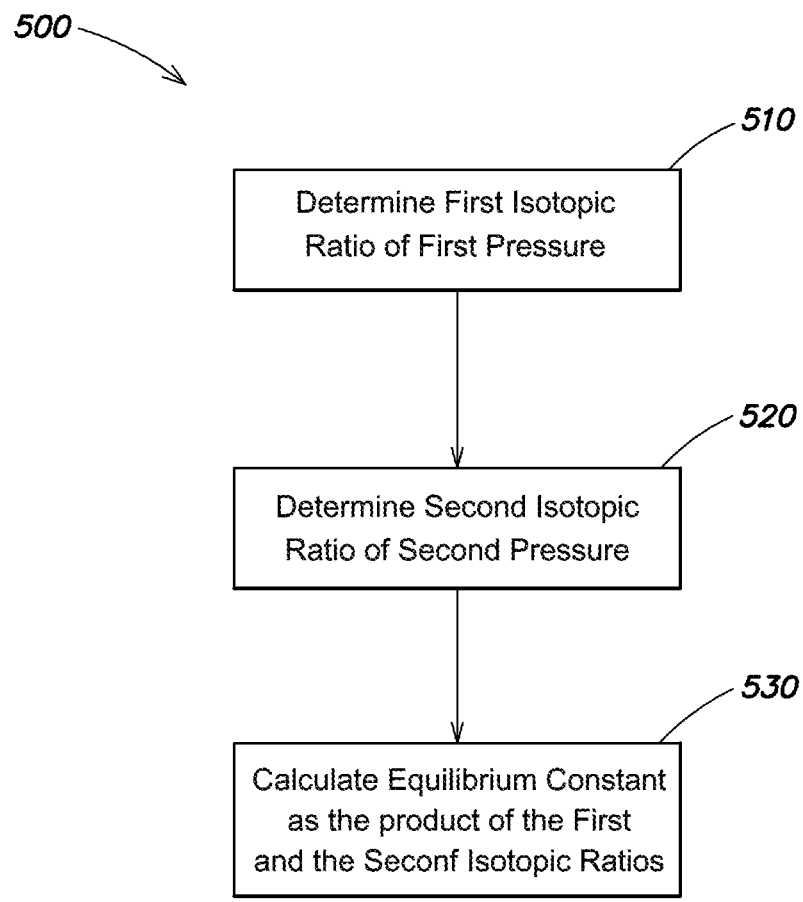
FIG. 5 is a flow diagram of an example calculation method.

FIG. 5 is a flow diagram of an example calculation method 500. At step 510, the analysis software 360 determines a first isotopic ratio at the first pressure based on the first sample spectrum. At step 520, the analysis software 360 executing on the computing system 350 determines a second isotopic ratio at the second pressure based on the second sample spectrum. At step 530, the analysis software 360 executing on the computing system 350 calculates the product of the first isotopic ratio and the second isotopic ratio to yield a super ratio that may be interpreted as an apparent equilibrium constant involving the clumped isotope.

For purposes of illustration, consider the molecule being studied is carbon dioxide, and the clumped isotope of interest is $^{13}C^{16}O^{8}O$ (abbreviated "638"). The apparent equilibrium constant, K, of clumped isotope 638 may be calculated using the above described example measurement cycle 400 and calculation method 400 as a product of isotopic ratios involving $^{12}C^{16}O^{8}O$ (abbreviated "628"), $^{12}C^{16}O^{16}O$ (abbreviated "626"), $^{13}C^{16}O^{16}O$ (abbreviated "636"), as:

$$K=([638]/[628])*([626]/[636]) \quad (1)$$

$$K=([638]/[636])*([626]/[628]) \quad (2)$$

Each isotopic ratio may be measured at a different pressure. As such, species may be probed at pressures that allow absorbance to be constrained (e.g., to a range of 0.1 to 1.0). For example, considering formula (1), the ratio [638]/[628] may be calculated based on a sample spectrum acquired at a first pressure (e.g., 0.2 mbar). At such pressure, line strengths of these species may differ by less than a predetermined amount, such that absorbance may be constrained substantially within the desired range. However, at the first pressure, absorbances of the species 638 or the species 636 may be greater than the desired range. Accordingly, [626]/[636] may be calculated based on a sample spectrum acquired at the second pressure (e.g., 0.02 mbar), such that both absorbances may be constrained substantially within the desired range The above described example instrument 300, measurement cycle 400 and calculation method 500 may avoid fractionation by maintaining the gaseous sample at very low pressures (e.g., below 2 mbar). Further fractionation may be discouraged by transferring a large fraction of the sample from the external bulb 340 to the sample cell 320. As described above, the volume of the sample cell 320 (e.g., 100 ml) may be an order of magnitude larger than the volume of the external bulb 340 (e.g., 11 ml), such that, when the gaseous sample in the external bulb is expanded into the sample cell, a large fraction will be transferred thereto. Furthermore, the low pressure environment may assure rapid mixing, which may also minimize any potential fractionation.

In summary, the above described example instrument 300, measurement cycle 400 and calculation method 500 may be utilized to determine an apparent equilibrium constant involving a clumped isotope in a gaseous sample by acquiring sample spectra of portions of the gaseous sample at different pressures, and utilizing pressure reduction to allow absorbance to be constrained. It should be understood that the instrument 300, measurement cycle 400 and calculation method 500 may be utilized together, individually, or in combination with other techniques, depending on the implementation. Further, it should be understood that various aspects may be modified, added to, removed, or otherwise changed depending on the implementation.

For example, while the above techniques describe using expansion to transfer portions of the gaseous sample from the external bulb 340 to the sample cell 320, it should be understood that such portions may be transferred in other manners. For instance, a pump may be utilized to actively transfer a portion of the gaseous sample.

Further, while the above techniques describe that the external bulb 340 is isolated from the sample cell 320, filled with the entire gaseous sample, and then a first portion of the gaseous sample is transferred from the external bulb to the sample cell, alternatively, the external bulb and sample cell may be filled together as part of a single operation. For example, the valve on the gas inlet port 322 may be opened and the external bulb 340 and sample cell 320 filled together with the gaseous sample to the first pressure. The first portion of the gaseous sample may be defined by closing the valve on the gas inlet port 322, to isolate the first portion within the sample cell. It should be understood that a variety of other variations may be employed to fill or evacuate the sample cell 320 with portions of the gaseous sample.

Further, while the above techniques describe use of a laser absorption spectrometer, it should be understood that at least some of the techniques may alternatively use another type of spectroscopy, which may not require a laser, for example, Fourier transform infrared spectroscopy.

Further, while it is described above that the computing system 350 executing the analysis software 360 is capable of controlling the valves on the ports 322, 324, 342, operating the laser 310, controlling the evacuation pump, etc., such that measurement cycle is fully automated, it should be understood that one or more of these devices may be manually controlled by an operator during the measurement cycle. Alternatively, one or more of these devices may be controlled by a separate system, such that the computing system 350 has a more limited role.

Still further, while specific examples of hardware-based instrumentation and software are discussed above, it should be understood that the techniques may be implemented using a variety of different types of hardware, software, and combination thereof. The hardware may include a variety of types of measurement instruments that may include, or be coupled to, computing systems having processors, memory chips, programmable logic circuits, application specific integrated circuits, and/or other types of components that support execution of software. The software may include executable instructions that implement applications stored in non-transitory electronic device-readable media, such as a volatile or persistent memory devices, hard-disks, or other data stores. Combinations of hardware and software may be adapted to suit different environments and applications.

In general, it should be understood that the above descriptions are meant to be taken only by way of example.

What is claimed is:

1. A method for measuring an apparent equilibrium constant involving a clumped isotope of a molecule in a gaseous sample, comprising:
   filling a sample cell of a laser absorption spectrometer with a first portion of the gaseous sample, the first portion of the gaseous sample being at a first pressure;
   acquiring a first sample spectrum of the first portion of the gaseous sample;
   transferring a second portion of the gaseous sample from an external bulb coupled to the sample cell into the sample cell, the second portion of the gaseous sample being at a second, different pressure;
   acquiring a second sample spectrum of the second portion of the gaseous sample, and
   calculating the apparent equilibrium constant involving the clumped isotope of the molecule based on the first sample spectrum and the second sample spectrum acquired at different pressures.

2. The method of claim 1, wherein the calculating comprises:
   determining a first isotopic ratio at the first pressure;
   determining a second isotopic ratio at the second pressure; and
   calculating the apparent equilibrium constant involving the clumped isotope as a product of the first isotopic ratio and the second isotopic ratio.

3. The method of claim 1, wherein the filling the sample cell with the first portion of the gaseous sample further comprises:
   filling the external bulb with the entire gaseous sample; and
   transferring the first portion of the gaseous sample from the external bulb to the sample cell.

4. The method of claim 3, further comprising:
   evacuating the external bulb and the sample cell; and
   isolating the external bulb from the sample cell, prior to filling the external bulb with the gaseous sample.

5. The method of claim 4, wherein the transferring the first portion of the gaseous sample comprises:
   allowing the gaseous sample to expand from the external bulb into the evacuated sample cell.

6. The method of claim 5, wherein the transferring the second portion of the gaseous sample comprises:
   isolating the external bulb from the sample cell, the external bulb to hold a remaining part of the gaseous sample;
   evacuating the sample cell; and
   allowing the remaining part of the gaseous sample to expand from the external bulb into the evacuated sample cell.

7. The method of claim 1, wherein the filling the sample cell with the first portion of the gaseous sample further comprises:
   filling the external bulb and the sample cell together with the entire gaseous sample; and
   isolating the external bulb from the sample cell, to isolate the first portion of the gaseous sample within the sample cell.

8. The method of claim 1, wherein the second pressure is lower than the first pressure.

9. The method of claim 1, wherein the external bulb is filled to an initial sample pressure, and the first pressure, second pressure, and initial sample pressure are selected as pressures that suppress isotopic fractionation.

10. The method of claim 9, wherein the first pressure is at least an order of magnitude lower than the initial sample pressure, and the second pressure is at least an order of magnitude lower than the first pressure.

11. The method of claim 1, wherein the laser absorption spectrometer includes a first laser and a second laser that operate in different spectral regions, wherein the first sample spectrum is acquired using the first laser, and the second sample spectrum is acquired using the second laser.

12. The method of claim 1, wherein the filling, transferring a first portion, acquiring a first sample spectrum, and acquiring a second sample spectrum is repeated using a reference gas in place of the gaseous sample, and the calculating calibrates the laser absorption spectrometer based on the reference gas.

13. The method of claim 1, wherein the molecule comprises carbon dioxide.

14. The method of claim 1, wherein the molecule comprises methane, nitrous oxide or carbon monoxide.

15. A method for measuring an apparent equilibrium constant involving a clumped isotope of a molecule in a gaseous sample, comprising:
   using a laser absorption spectrometer to determine a first isotopic ratio of the molecule from a first portion of the gaseous sample at a first pressure;
   using the laser absorption spectrometer to determine a second isotopic ratio of the molecule from a second portion of the gaseous sample at a second pressure, the second pressure being different than the first pressure; and
   calculating the apparent equilibrium constant involving the clumped isotope as a product of the first isotopic ratio and the second isotopic ratio.

16. The method of claim 15, further comprising:
   filling an external bulb coupled to a sample cell of the laser absorption spectrometer with the entire gaseous sample, the first portion and the second portion being transferred from the external bulb.

17. The method of claim 16, wherein the external bulb is initially at an initial sample pressure, and the first pressure is lower than the initial sample pressure, and the second pressure is lower than the first pressure.

18. The method of claim 16, further comprising:
   transferring the first portion of the gaseous sample from the external bulb to the sample cell by allowing the gaseous sample to expand into the sample cell;
   evacuating the sample cell; and
   transferring the second portion of the gaseous sample from the external bulb to the sample cell by allowing a remaining part of the gaseous sample in the external bulb to expand from the external bulb into the sample cell.

19. The method of claim 15, further comprising:
   filling an external bulb coupled to a sample cell of the laser absorption spectrometer together with the sample cell together with the entire gaseous sample; and isolating the external bulb from the sample cell, to isolate the first portion of the gaseous sample within the sample cell.

20. The method of claim 15, wherein the molecule comprises carbon dioxide, methane, nitrous oxide or carbon monoxide.

21. An instrument for measuring an apparent equilibrium constant involving a clumped isotope in a gaseous sample, comprising:
  a spectrometer including:
    a sample cell having an inlet port and outlet port, and
    an external bulb coupled to the inlet port, the external bulb holding at least some of a gaseous sample, and
    a plurality of controllable valves, the plurality of controllable valves including a valve disposed at the inlet port of the sample cell; and
  a computing system having a processor configured to execute analysis software that controls the spectrometer, the analysis software when executed operable to:
    operate at least one of the plurality of controllable valves to transfer a first portion of the gaseous sample to the sample cell, the first portion of the gaseous sample being at a first pressure,
    use the spectrometer to acquire a first sample spectrum of the first portion of the gaseous sample,
    operate the valve disposed at the inlet port to transfer a second portion of the gaseous sample from the external bulb to the sample cell, the second portion of the gaseous sample being at a second, different pressure,
    use the spectrometer to acquire a second sample spectrum of the second portion of the gaseous sample, and
    calculate an apparent equilibrium constant involving the clumped isotope of the molecule based on the first sample spectrum and the second sample spectrum acquired at different pressures.

22. The apparatus of claim 21, further comprising:
  an evacuation pump coupled to the outlet port, and
  wherein the analysis software when executed is further operable to use the evacuation pump to evacuate the sample cell.

23. The apparatus of claim 21, further wherein the analysis software that when executed is operable to calculate is further operable to:
  determine a first isotopic ratio at the first pressure;
  determine a second isotopic ratio at the second pressure; and
  calculate the apparent equilibrium constant involving the clumped isotope as a product of the first isotopic ratio and the second isotopic ratio.

24. The apparatus of claim 21, wherein the second pressure is lower than the first pressure.

25. The apparatus of claim 21, wherein the spectrometer includes a first laser and a second laser that operate in different spectral regions, wherein the first sample spectrum is acquired using the first laser and the second sample spectrum is acquired using the second laser.

26. The apparatus of claim 21, wherein the molecule comprises carbon, dioxide methane, nitrous oxide or carbon monoxide.

* * * * *